United States Patent [19]
Von Bieren

[11] 3,936,160
[45] Feb. 3, 1976

[54] INTERFEROMETER FOR THE MEASUREMENT OF WAVEFRONT SECTIONS OF GENERAL IMAGING SYSTEMS INCLUDING THE HUMAN EYE

[76] Inventor: Karlheinz Von Bieren, Tudor Hill Laboratory, F.P.O., N.Y. 09560

[22] Filed: Oct. 15, 1973

[21] Appl. No.: 406,596

[52] U.S. Cl. .................. 351/6; 356/109; 356/113
[51] Int. Cl.² ............................................. A61B 3/10
[58] Field of Search ........ 351/9, 6; 356/106 R, 113, 356/124, 109

[56] References Cited
UNITED STATES PATENTS

| | | |
|---|---|---|
| 1,565,533 | 12/1925 | Twyman et al. ................. 356/109 |
| 1,824,668 | 9/1931 | Hasselkus et al. ............... 356/106 R |
| 2,878,722 | 3/1959 | Hopkins et al. ..................... 356/113 |
| 3,536,383 | 10/1970 | Cornsweet et al. .................... 351/6 |
| 3,600,098 | 8/1971 | Mohrman .............................. 351/6 |
| 3,639,041 | 2/1972 | Cornsweet .............................. 351/6 |

*Primary Examiner*—Harold A. Dixon
*Attorney, Agent, or Firm*—Gipple & Hale

[57] ABSTRACT

An interferometer method for measuring aberrations in a lens system by analysis of a Fourier transform pattern generated by the lens system and the embodiment of this principle for the measurement of aberrations in the human eye and in the general imaging system.

10 Claims, 5 Drawing Figures

INTERFEROMETER FOR THE MEASUREMENT OF WAVEFRONT SECTIONS OF GENERAL IMAGING SYSTEMS INCLUDING THE HUMAN EYE

BACKGROUND OF THE INVENTION

This invention relates to a method and apparatus for measuring wavefront sections of optical imaging systems and accomplishes this object without complex and expensive readout equipment. While directed specifically to measurement of wavefronts in the human eye, the invention is not limited in its application as an eye interferometer, since an additional object of the invention is its use as a fan trace interferometer for wavefront investigation of photographic objectives, reproduction lenses, telescopes, microscopes, enlarger lenses, and other imaging systems.

The human eye is an optical system characterized by aberrations of several types. One contributing factor to these aberrations is the fact that the human eye is not a rotationally symmetric optical system, because the fundus, where the vast majority of all vision takes place, is not located on the optical axis of the refracting elements of the eye, which optical axis makes an angle of 4° to 7° with the axis of best vision.

Due to the lack of coincidence of the optical axis with the axis of best vision of the eye lens system, leading to a rotationally asymmetric optical system with two perpendicular planes of symmetry, a large number of aberrations occur in the human eye optical system. The consequence of such aberrations is imperfect vision, ranging widely in degree of impairment of an individual's vision. So-called star rays, observed by most people to be emanating radially from a bright star at night, result from eye optical system aberrations.

Allviar Gullstrand was able to show mathematically that these star rays are due to aberrations caused by the optical system of the human eye. Helmholz also found that eyes without lenses, where the lenses have been removed due to cataracts, don't see these star rays.

Determination of aberrations of the type described require measurement of the phase of the light oscillation of a wavefront along the path of the wavefront where ray paths may be identified.

One crucial property of an interferometer is the provision to allow the measurement of the phase of the light oscillation of a wavefront. Because of the high frequency of the light oscillation, this measurement can only be achieved through comparison with a reference wave front of the same frequency. Another important property — as far as an interferometer for the determination of lens aberrations is concerned — relates to the fact that the phase measurement must be performed at a position along the path of the wavefront where ray paths may be identified. This allows it to trace the ray through the optical system and thus relate the phase measurement of the interferometer with a ray or a wavefront section which penetrates the aperture at a well defined location. For instance, if the phase measurement is performed at or near a caustic, it is not possible to determine the phase contributions of individual aperture sections, since the interferometer in this case measures the phase of the light oscillation which results from the vector addition of a large number of rays.

Therefore, whenever objects are "imaged" onto the retina, a ray convergence in the form of a caustic results. In fact, the size of the caustic is directly related to the aperture necessary to provide this resolution by the Helmholz-Lagrange formula, which may be interpreted as a sort of uncertainty relation: resolution size times aperture size is a constant; thus good resolution (small size) necessitates a large aperture.

Recent opthalmologic research indicates that cataracts introduce primarily phase errors in the various ray paths, while amplitude effects are not critically large. (Optical Engineering, "Holographic Phase Compensation Techniques Applied to Human Cataracts," Jan/- Feb. 1973. ) Therefore, at least in principal, it is possible to compensate the phase errors of the cataract with an appropriate phase plate. Since holography cannot be applied to the in-vivo eye, these phase errors first have to be measured, and since it is absolutely necessary to assume a deviation from the spherical or toric shape of the wavefront, an instrument with interferometric resolution is required. On the other end of the scale, as shown by way of the star rays, even the resolution of the perfect eye could be improved, which would lead to improved night vision.

The inventive interferometer satisfies both interferometer requirements. It can be shown that there are only two rays intersecting at any point on the retina, and the interference of these two ray bundles generates a characteristic multi-stripe pattern which allows the phase measurement. Therefore, there is no caustic being generated on the retina, and no ambiguity about the origin of the phase error exists. Thus the inventive interferometer allows it to measure the vector contribution of all rays of a wavefront in the focal point where the caustic is normally formed. An important property of the eye interferometer is that a measurement in the eye can only be performed on the retina as the space between the retina and the eye lens is not accessible.

However, in testing camera lenses, for instance, a similar situation exists, in that the space between the film plane and the objective in many cameras is not accessible, and the inventive interferometer may be useful in those cases. However, if the situation requires a phase measurement outside the focal plane, the inventive interferometer works just as well.

Another important property of the interferometer is the complete absence of any phase ambiguity. It is well known that an interferometer which provides phase information in the form of a contour map of the wavefront has a serious phase ambiguity. While it is easily established that the phase differential between adjacent contour lines is $2\pi$, it is difficult to determine whether the phase is retarding or advancing in crossing from one line to the next. As the interferometer apparatus and method in the invention indicate, no such problem exists in the fan trace interferometer or its equivalent application, the eye interferometer.

Since corrective treatment first requires diagnostic measurement, one object of this invention is to measure phase errors of eye-optical defects, including mild cataracts to supply information needed to construct a suitable compensatory lens. In addition, the resolution of the perfect eye is capable of improvement after a proper measurement of eye aberrations by the invention.

DESCRIPTION OF THE PRIOR ART

Interferometers for the investigation of wavefronts can be grouped into two distinct categories. The first group basically utilizes the division of the wavefront principle as demonstrated by Young's historical experiment which established the wave nature of light. Other division of wavefront principle representatives are Michelson's stellar interferometer and Rayleigh's inteferometer for the precision gas index measurement.

A second category is based on the division of amplitude principle. In the large variety of interferometers that belong to this group, there are two basic types which serve to investigate lens aberrations; namely, the Twyman-Green interferometer which is disclosed in British Pat. No. 103,832 and the Bates shear interferometer which is disclosed in 59 Proceedings of Physics Society 940 (London 1947). The Twyman-Green interferometer, which is a variation of the Michelson interferometer, is used in testing optical systems in autocollimation. Due to the autocollimination feature of this interferometer, the exact interpretation of aberrations as they appear in interferograms presents problems. The Bates shear interferometer has attempted to overcome this difficulty, in that a wavefront and its sheared replica interfere to produce straight fringes. The movement of this fringe pattern as a function of the shear parameter makes it possible to compute the wavefront slope. This process is extremely tedious, as the wavefront has to be measured and computed for each point individually. In addition, the process is only applicable for large aperture systems where there is room to accommodate the interferometer between the last refracting or reflecting surface and the focal point of the wavefront.

Other developments have been made to accurately measure lens and eye focusing properties. U.S. Pat. No. 3,136,839 discloses a survey of early opthomoscope methods which have been utilized in the field. In particular, U.S. Pat. No. 3,536,383 discloses a method and apparatus for measuring the refracted power of the eye. This reference is based on the principle that, with the eye focused on infinity, all parallel rays impinging on the lens will be deflected to the same point on the retina, assuming no aberrations in the lens. An optical set-up is devised to provide a vibrating pin ray of light which is always parallel to the optic axis of the eye lens to scan across the lens. If the image produced on the retina moves, then the lens is introducing some phase difference between the different optical paths. Another U.S. Pat. No. 3,639,041 discloses a method and apparatus for obtaining a map of the depth of various points of the fundus from an arbitrary point on the lens. When the eye is focused at a given distance, the image is of two laterally displaced sources or images on the retina by varying the distance from the eye to the aperture to make the two images coincide. This same procedure is repeated for different positions on the retina with the different values of distance from the aperture to the eye at perfect focusing providing information on the distances from the eye to the different points on the retina. The prior art which has been used necessitates complex and expensive read-out equipment to determine when and if images overlap.

Applicant's fan trace interferometer is based upon the division of wavefront principal and, like the shear interferometer, it measures the wavefront slope, with the difference being that the interpretation of the interferometer plot is extremely simple. The present invention requires no computation since the interferometer provides an automatic calibration, and alignment requirements for the instrument are reduced to a bare minimum.

SUMMARY OF THE INVENTION

The interferometer invention is based upon the fact that a Fourier transform intensity pattern remains stationary when the input function is shifted, provided there are no aberrations in the optical system, so that the detection of any pattern shift and its measurement provides aberrational information. The measured motion of the Fourier transform display in the back focal plane of a lens system measures the degree of phase error introduced by aberrations in the lens imaging system. Consequently, the invention furnishes, along a line of scan of the lens system under study, a measurement of the wavefront within the lens system under study.

DETAILED DESCRIPTION OF THE DRAWINGS

In a general optical Fourier transform layout, the input plane, which is illuminated by a coherent or quasi-coherent monochromatic light contains a transmission function with the well known Fourier transform.

Figure 1:
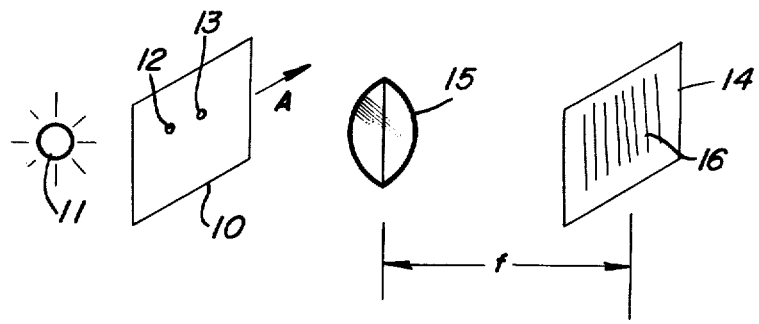
FIG. 1 shows a schematic diagram of a known interferometer.

In a simple example shown in FIG. 1, the input plane 10 consists of an opaque surface perforated by two pinholes 12 and 13, with a fixed spacing in a lateral dimension, and is illuminated by a coherent or quasi-coherent monochromatic light 11. The lends 15, constituting the imaging system and having an equivalent focal length f under study, produces a Fourier transform display in the back focal plane 14, located a distance f from the lens 15. Thus, the display in the back focal plane 14 where the Fourier transform is displayed consists of a system of parallel equidistant stripes 16. As the double pinhole apertures 12 and 13 are moved laterally in the direction shown by arrow A, the stripe system or pattern 16, at a particular point of observation in the back focal plane 14, remains stationary if the imaging system provides a stigmatic ray convergence for that point. If, on the other hand, the imaging system produces phase errors, the lateral movement of the stripe system is a direct indication of the phase errors.

Figure 2:
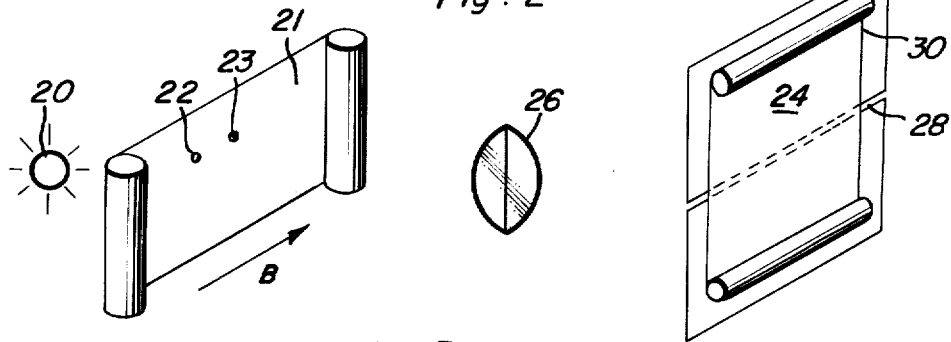
FIG. 2 shows a schematic diagram of a lens measuring interferometer of the present embodiment.

A method and apparatus for recording any lateral movement of the stripe system 16 produced from the previously mentioned imaging system is shown in FIG. 2.

In the invention, the lateral movement of the Fourier stripe pattern 16 may be recorded on photographic film 24 with the principle previously disclosed. The interferometer requires only the insertion of a double-pinhole aperture into the ray path between the light source and the Fourier transform plane to measure the aberrations of a lens system. As shown by FIG. 2, an opaque signal film 21 having two pinholes 22 and 23, as shown by arrow B, moves synchronously, in either a continuous manner or in discrete steps, in a perpendicular travel direction to that of a recorder film 24. A source of monochromatic, coherent or quasi-coherent light 20 of wavelength λ from either a candescent of incandescent source illuminates the pinholes 22 and 23 and through the imaging system of lens 26 under-test a Fourier pattern is formed. A slit 28 in mask 30 allows a section of the light pattern 16 to expose the photographic or recording output film 24, which records the aberration function of the imaging system. Owing to the synchronous movement of both films the shift parameter appears as a coordinate on the output film to form an aberrational record of the wavefront section on the output film. It is also possible to investigate the wavefront behavior in the perpendicular direction by a change in the orientation of the pinhole connecting line, output slit and direction of output film travel of 90°. The wavefront slope in any direction and along any track across the wavefront may be recorded at any point in the output plane by a proper choice of the geometric parameters of input and output.

Figure 3:
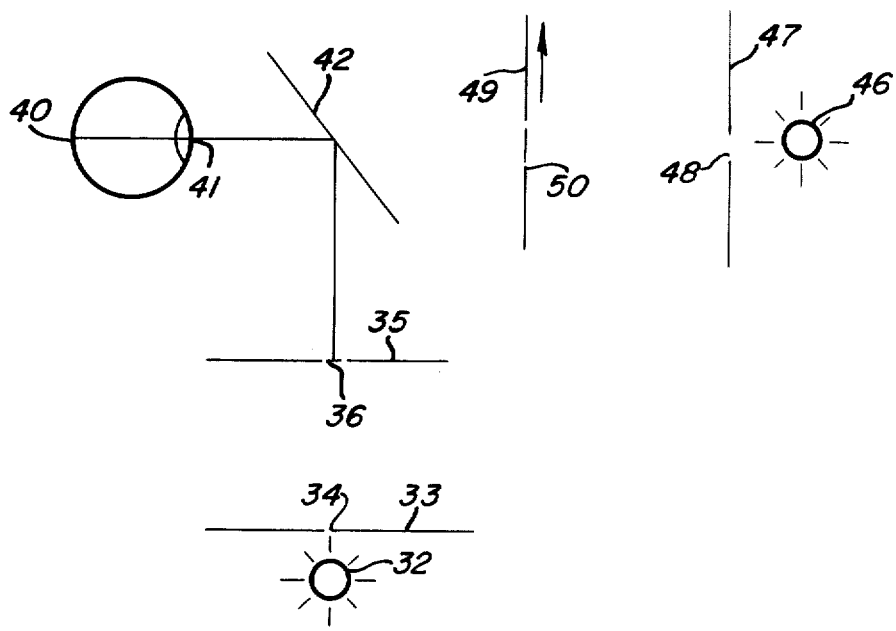
FIG. 3 shows a schematic diagram of an interferometer for measuring and recording wavefronts in the human eye.

In the eye testing embodiment shown in FIG. 3, the subject actually sees the movement of the Fourier test pattern relative to the reference pattern, which movement provides a point-by-point measurement of the wavefront in the human eye with interferometric resolution.

The principle of this embodiment is based upon the fact that the intensity pattern of the Fourier transform remains stationary on the retina when the aperture and light source are moved laterally across the aperture of the eye, provided that the relaxed eye is emmetropic.

In this embodiment, a light source 32, a first light input plane 33, with a single pinhold aperture 34, a second light input plane 35, with a double pinhole aperture 36, are combined to produce a Fourier reference transform pattern on the retina 40 of the eye by reflecting the pattern onto the retina through a partially transparent mirror 42. A second Fourier measurement pattern is projected through the transparent mirror 42. The measurement pattern is produced by light source 46, a first movable plane 47 with a single pinhole 48, and a second movable plane 49, having a double pinhole 50. The second measurement pattern is moved across the aperture of the eye in certain increments, the size of which is determined by the aberration of the eye. The principle of the measurement system is based on the fact that the intensity pattern of the Fourier transform intensity patterns remains stationary on the retina when the measurement pattern is moved laterally across the eye aperture 41, if there are no aberrations generated in the eye.

In practical application both Fourier patterns are brought into coincidence with the double pinholes 50, being positioned so as to illuminate the edge of the iris. The movable planes 47 and 49 are moved laterally by a given amount ΔX until the two patterns start to deviate from coincidence. At this point the first movable plane 47 with its associated single pinhole 48 is moved laterally until the two patterns coincide again. This lateral movement of the single pinhole 48 changes the phase relationship at the double pinhole 50 by a given amount which can be measured precisely, and which is a direct measure of the phase error caused by the refracting elements of the eye. Then both the single and double pinholes of the movable measurement means are moved again in the same direction until coincidence is lost. Then the measuring steps are repeated so that the complete wavefront of the eye can be sampled and measured in this manner.

This aberrations of the eye can be measured without difficulty with this device. However, it is anticipated that complicated wavefronts caused by certain cataracts may be measured as well with a possibility of correction by higher order refractive elements.

Figure 4:
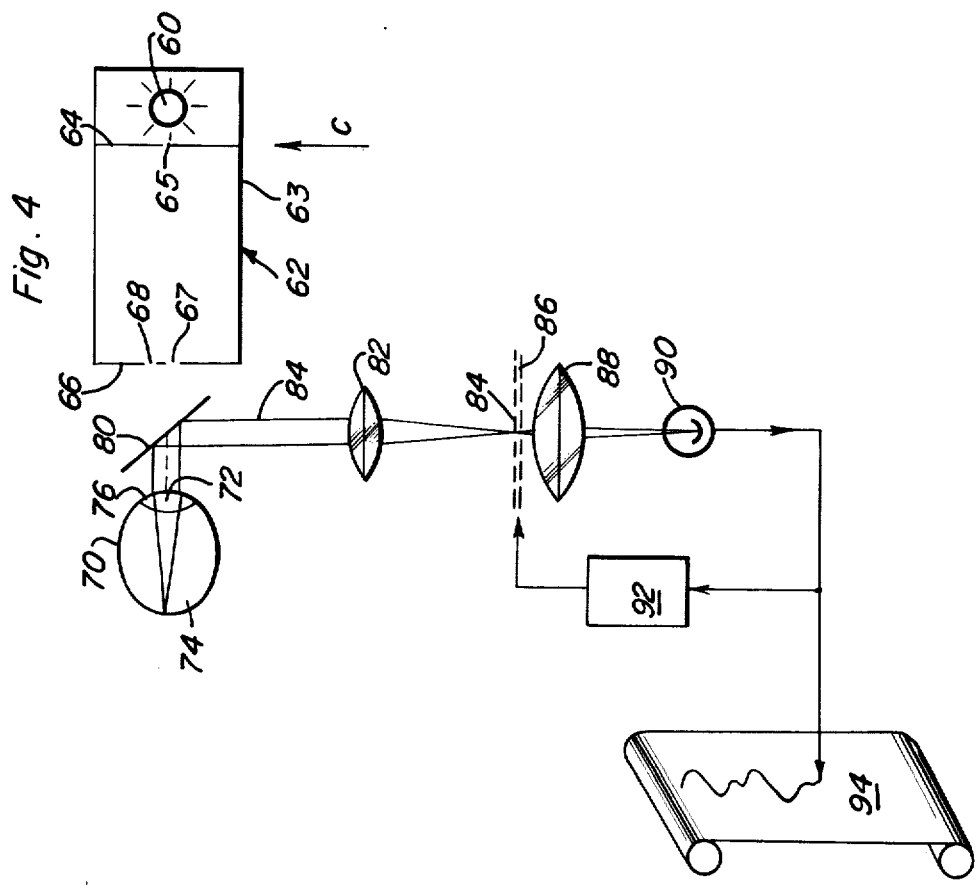
FIG. 4 shows a schematic diagram of another interferometer embodiment for measuring and recording wavefronts in the lens of the human eye.

FIG. 4 shows another embodiment of the invention in which the Fourier pattern may be moved laterally across the eye, and the output signal records eye aberrations in a high-speed recorder or a computer. In this embodiment, a source of monochromatic, coherent, or quasi-coherent light 60 (from either a candescent or incandescent source) is positioned inside a transmission means 62, comprising a housing 63 having an input plane 64 with a pinhole 65 and a second input plane 66, with double pinhole apertures 67 and 68 located sufficiently close to the eye 70 so that the eye 70 cannot focus on the double pinhole apertures 67 and 68. The eye 70 has a lens 72, a retina 74, and an iris 76, positioned in front of the transmission means 62, which transmits the pattern into the eye 70 through a beamsplitter 80 which may, for example, be a partially transparent silvered mirror.

An imaging lens 82 focuses the Fourier transform intensity pattern from the retina, which is reflected back from the eye through the beamsplitter 80 and the imaging lens 82 onto the aperture 86. This pattern 84 is the Fourier-transform of aperture 65 and consists of a system of parallel equidistant stripes. The stripe pattern is projected from the imaging lens onto a reading mask 86 which, under optimum conditions, allows all or none of the image intensity pattern to be transmitted thereto.

Located behind the reading mask 86 is a collective lens 88 which gathers the light transmission through the reading mask 86 and directs the light to a detector system 90. The detector system 90 preferably is a photo cell which measures the misalignment of the stripe pattern 84 with the reading mask 86 and provides control voltage to align the reading mask 86 and the image intensity pattern 84. The control voltage activates a servo-mechanism 92, which is connected to the reading mask 86 through suitable linkage not shown, to movably shift the reading mask 86 to regulate the intensity of light passed through the reading mask into the collective lens 88. The servo-mechanism 92 also controls the recording of the phase misalignment on a recorder 94, which may be a high-speed recorder or a computer. In the drawing a stylus is shown to provide a visual indication on the recording device. In a practical application, the transmission means 62 is located so as to illuminate the edge of the iris 76 of the eye 70. Next, the transmission means is moved laterally in the plane indicated by arrow C until the entire lens 72 of the eye 70 is traversed and measured.

Figure 5:
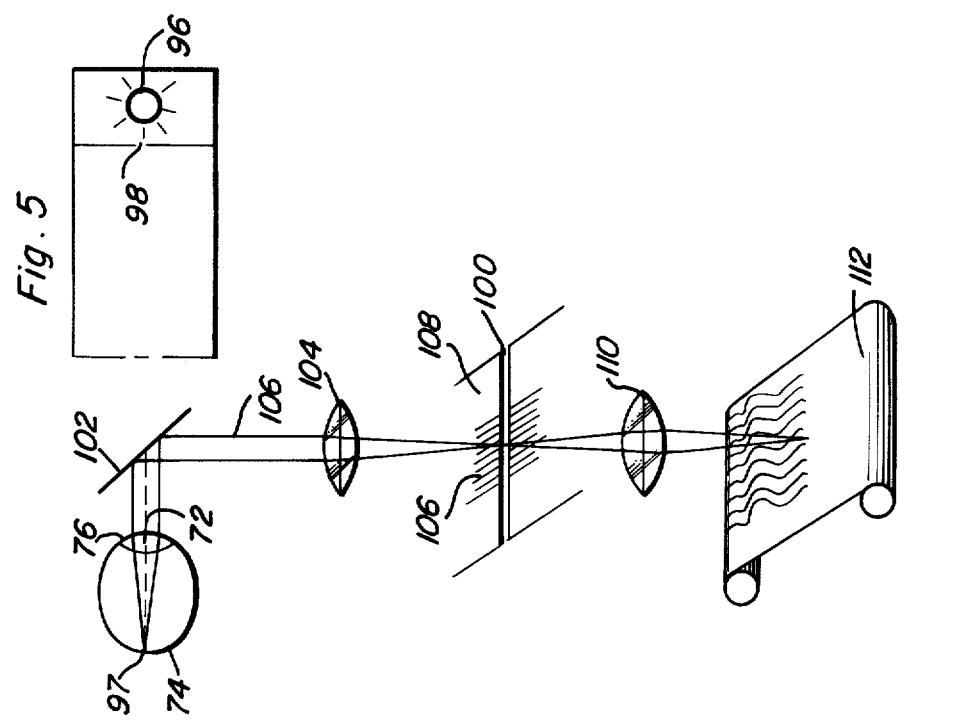
FIG. 5 shows a schematic diagram of another embodiment of the invention, with the output information in the form of light imaged and recorded on high-speed film.

Yet another embodiment of the invention is shown in FIG. 5. FIG. 5 shows a source of monochromatic, coherent or quasi-coherent light 96, from either a candescent or an incandescent source which produces a Fourier intensity pattern 97 as previously set forth. The double pinhole 98 is located sufficiently close to the eye 70 so that the eye 70 cannot focus on the aperture. The eye 70, having a lens 72, a retina 74, and an iris 76, is directed at a beamsplitter 102, which is constructed as previously described. An imaging lens 104 forms an image 106 of the Fourier transform intensity pattern which is reflected from the retina 74 of the eye 70 by beamsplitter 102 onto a mask 108, having a readout slit 100. Light passing through the slit 100 is gathered by relay lens 110, which images the slit information onto recording film 112. The recording film then visually records the aberrations of the eye. The recording film may be high-speed film moving in the direction shown.

While the preferred embodiment of the invention has been disclosed, it is understood that the invention is not limited to such an embodiment since it may be otherwise embodied in the scope of the appended claims.

What is claimed is:

1. An interferometer for measuring aberrations in a lens system comprising movable means for generating a Fourier transform pattern in an eye, means for reflecting said pattern in said eye onto a mask, said mask defining slotted aperature means therein to allow a portion of said reflected pattern to pass therethrough onto a recording means, an imaging lens positioned in the path of said reflected pattern between said reflecting means and said mask and a relay lens positioned in the path of said reflected pattern between said mask and said recording means, said recording means comprising high speed film which records the aberrations of the eye.

2. An interferometer for measuring wavefront sections of an imaging system comprising a transparent reflective means including a beam splitter, a first fixed means for transmitting a coherent light input pattern against said reflective means to reflect said pattern into an eye, where the Fourier transform of the input pattern is generated, a second movable means for transmitting an input pattern through said beam splitter into an eye to form a coincidence Fourier transform pattern with said first means.

3. An interferometer for measuring aberrations in a lens system comprising means for transmitting a coherent light input pattern into an eye, where the Fourier transform of said pattern is generated means for reflecting said pattern in said eye onto a mask, an imaging lens positioned in the path of said reflected pattern between said reflecting means and said mask, said mask defining aperture means therein to allow at least a portion of said reflected pattern to pass therethrough onto light responsive means, a collecting lens positioned in the path of said reflected pattern between said mask and said light responsive means, said light responsive means controlling a servo-mechanism connected thereto to selectively vary the amount of light passing through said mask and to simutaneously record the lens aberration on a recording means, such as a computer.

4. An interferometer for the measurement of lens aberrations by analyzing of a Fourier transform pattern generated by a lens system, from aperture sections which are emitting coherent light, said lens system comprising a human eye with movable means for generating a Fourier transform pattern in said eye and means to record the movement of this pattern contained in the light reflected from the retina onto a storage medium.

5. An interferometer as claimed in claim 4 including a stationary means, said stationary means being adapted to simultaneously generated a second Fourier transform pattern for calibration purposes.

6. A interferometer as claimed in claim 4 wherein said lens system comprises a general imaging system such as a photographic camera objective with movable means for generating a Fourier transform pattern through said imaging system and recording means.

7. A method for the interferometric measurement of wavefront sections in a human eye using two Fourier transform generating mechanisms each of which has a quasi-coherent light source and a multiple pinhole input plane, comprising the steps of generating a reference Fourier transform pattern on the retina of the eye, generating a second Fourier transform pattern on the retina so that first and second patterns are brought into coincidence, moving said measurement pattern generator a given distance until the two patterns start to deviate from coincidence, moving said measurement quasi-coherent light source until the two patterns coincide again and measuring the phase change relationship of the light source and multiple pinhole input plane.

8. An interferometer as claimed in claim 7, wherein the translation process and the coincidence alignment process are automated, using visible light for the Fourier transform generation and readout steps with the resulting wavefront function being fed into a storage device.

9. An interferometer as claimed in claim 8 wherein said translation process and the coincidence alignment process are automated using infra red light for the Fourier transform generation and readout steps.

10. A method of taking interferometric measurement of wavefront sections in a human eye using two Fourier transform pattern mechanisms each of which has a pinhole light aperture and a multiple-pinhole input plane comprising the steps of projecting a reference Fourier transform pattern onto the retina of the eye, projecting a second measurement Fourier transform pattern onto the retina so that said first and second patterns are brought into coincidence, moving said measurement pattern a given distance until the two patterns start to deviate from coincidence, moving said measurement mechanism pinhole aperture until the two patterns coincide again, and measuring the phase change relationship of the pinhole aperture and multiple-pinhole input plane.

* * * * *